United States Patent [19]
Cliffe et al.

[11] Patent Number: 5,627,177
[45] Date of Patent: May 6, 1997

[54] PIPERAZINE DERIVATIVES

[75] Inventors: Ian A. Cliffe; Christopher I. Brightwell; Howard L. Mansell, all of Slough; Alan C. White, Staines, all of England

[73] Assignee: John Wyeth & Brother, Ltd., United Kingdom

[21] Appl. No.: 446,601

[22] PCT Filed: Dec. 24, 1993

[86] PCT No.: PCT/GB93/02660

§ 371 Date: May 24, 1995

§ 102(e) Date: May 24, 1994

[87] PCT Pub. No.: WO94/15919

PCT Pub. Date: Jul. 21, 1994

[30] Foreign Application Priority Data

Jan. 6, 1993 [GB] United Kingdom ............ 9300195

[51] Int. Cl.⁶ ............ A61K 31/55; C07D 487/12
[52] U.S. Cl. ............ 514/212; 514/210; 514/252; 514/254; 540/481; 540/598; 540/599; 544/362; 544/363; 544/371; 544/373
[58] Field of Search ............ 540/481, 598, 540/599; 544/362, 363, 371, 373; 514/210, 212, 252, 254

[56] References Cited

U.S. PATENT DOCUMENTS

| | | | |
|---|---|---|---|
| 5,169,845 | 12/1992 | Cliffe et al. | 514/212 |
| 5,382,583 | 1/1995 | Cliffe et al. | 514/252 |

FOREIGN PATENT DOCUMENTS

| | | |
|---|---|---|
| 0512755A2 | 4/1992 | European Pat. Off. . |
| 2230780 | 10/1990 | United Kingdom . |
| 2230781 | 10/1990 | United Kingdom . |
| WO9203426 | 3/1992 | WIPO . |
| WO9311122 | 6/1993 | WIPO . |

OTHER PUBLICATIONS

M. El–Bermawy et al., *Medicinal Chemistry Research* 2:88–95 (1992).

*Primary Examiner*—Joseph McKane
*Assistant Examiner*—Richards Myers, Jr.
*Attorney, Agent, or Firm*—R. F. Boswell, Jr.

[57] ABSTRACT

Piperazine derivatives of formula (I) and their pharmaceutically acceptable salts are $5\text{-}HT_{1A}$ binding agents and may be used, for example, as anxiolytics. In the formula, A is an optionally substituted alkylene chain, Z is a specified bicyclic nitrogen containing heteroaromatic radical, R is hydrogen or lower alkyl, $R^1$ is aryl or aryl(lower)alkyl and $R^2$ and $R^3$ are hydrogen or specified organic radicals or $-NR^2R^3$ represents a heterocyclic ring.

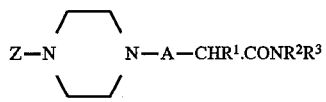

(I)

13 Claims, No Drawings

PIPERAZINE DERIVATIVES

This application is a National phase filing under 37 USC § 371 of PCT/GB93/02660 filed Dec. 24, 1993.

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

GB 2230781-A and GB 2230780-A disclose some piperazine derivatives which exhibit $5\text{-HT}_{1A}$ receptor affinity.

The novel compounds of the invention are those of the general formula

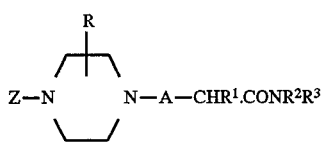

and the pharmaceutically acceptable acid addition salts thereof.

In formula (I)

A is an alkylene chain of 1 or 2 carbon atoms optionally substituted by one or more lower alkyl groups, Z is a bicyclic nitrogen containing heteroaromatic radical selected from the group consisting of optionally substituted indolyl, isoindolyl, quinolinyl, isoquinolinyl, indazolyl and benzotriazolyl, R represents hydrogen or one or two same or different lower alkyl groups, $R^1$ is an aryl radical or an aryl(lower)alkyl radical, $R^2$ is hydrogen or lower alkyl and $R^3$ is hydrogen, an alkyl group of 1 to 10 carbon atoms, cycloalkyl of 3 to 12 carbon atoms, cycloalkyl(lower)alkyl, aryl or aryl(lower)alkyl or $R^2$ and $R^3$ together with the nitrogen atom to which they are both attached represent a saturated heterocyclic ring which may contain a further hetero atom (eg an azetidino, pyrrolidino, piperidino, hexahydroazepino, heptamethyleneimino, morpholino or piperazino ring which may be optionally substituted by lower alkyl, aryl or aryl(lower)alkyl).

The term "lower" as used herein means that the radical referred to contains 1 to 6 carbon atoms. Preferably such radicals contain 1 to 4 carbon atoms. Examples of alkyl radicals are methyl, ethyl, propyl, isopropyl, butyl, isobutyl, sec-butyl, tert-butyl, pentyl and isopentyl. When $R^3$ is an alkyl radical a particularly preferred radical is a tertiary alkyl radical such as tert-butyl. Examples of cycloalkyl groups of 3 to 12 carbon atoms include cyclopropyl, cyclobutyl, cyclopentyl, cyclohexyl and cycloheptyl. Cycloalkyl groups also include bicyclic, tricyclic and tetracyclic groups eg adamantyl.

When used herein "aryl" means an aromatic radical having 6 to 12 carbon atoms (e.g. phenyl or naphthyl) which optionally may be substituted by one or more substituents commonly used in medicinal chemistry, eg substituents such as lower alkyl, lower alkoxy, lower alkylthio, halogen, trifluoromethyl, nitro, carbalkoxy, carboxamido, cyano, amino, (lower)alkylamino and di(lower)alkylamino.

Examples of aryl(lower)alkyl include, for example, benzyl in which the phenyl group may be substituted as defined above.

The bicyclic nitrogen containing heteroaromatic radical Z may be unsubstituted or substituted by, for example, one or more same or different substituents selected from lower alkyl, halogen, halo(lower)alkyl (eg trifluoromethyl), nitro, nitrile, oxo, hydroxy, (lower)alkoxy, hydroxy(lower)alkyl, (lower)-alkoxy(lower)alkyl, lower alkanoyloxy(lower)alkyl, lower alkylcarbonyl, (lower)alkylcarbonyl(lower)alkyl, carboxamido, (lower)alkoxy carbonyl, amino, (lower)alkylamino or di(lower)alkylamino. A particularly preferred substituent is (lower)alkoxycarbonyl e.g. —CO.O.CH$_3$.

Where Z is an optionally substituted indolyl or indazolyl radical, the radical is preferably linked via position 4 or 7 (most preferably via position 4) to the nitrogen atom of the piperazine ring. When Z is an optionally substituted quinolinyl or isoquinolinyl radical, the radical is preferably linked via position 5 or 8 (most preferably via position 5) to the nitrogen atom of the piperazine ring.

Examples of preferred compounds are (A) those in which A is ethylene (B) those in which $R^2$ is hydrogen and $R^3$ is tert-alkyl or cycloalkyl (C) those in which $NR^2R^3$ represents a piperidino or hexahydroazepino ring (D) those in which Z is optionally substituted indolyl, particularly indol-4-yl optionally substituted by, for example methoxycarbonyl in, for example the 2-position (E) those in which R is hydrogen (F) those in which $R^1$ is phenyl The compounds of the invention may be prepared by methods known in the art from known starting or starting materials that may be prepared by conventional methods. One method comprises alkylation of a piperazine compound of formula

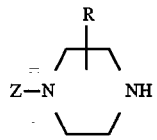

(where Z and R are as defined above) with an alkylating agent providing the group

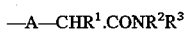

(where A, $R^1$, $R^2$ and $R^3$ have the meanings given above)

The alkylating agent may be, for example a compound of formula

where A, $R^1$, $R^2$ and $R^3$ are as defined above and X is a leaving group such as halogen or an alkyl- or arylsulphonyloxy group. Alternatively the alkylating agent may be an unsaturated compound of formula

(where $R^1$, $R^2$ and $R^3$ are as defined above) and the compound of formula (V) is reacted with the piperazine of formula (II) by means of a Michael reaction.

The starting piperazine of formula II may be prepared, for example, by the methods disclosed in EP-A-138280 and EP-A-372657.

In an alterative method of preparing the compounds of the invention an amine of formula

(where $R^2$ and $R^3$ are as defined above) is acylated with an acid of formula

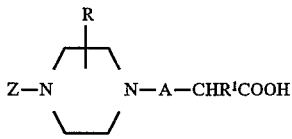

(where Z, A, R and $R^1$ are as defined above) or with an acylating derivative thereof. Examples of acylating derivatives include the acid halides (eg acid chlorides), azides, anhydrides, imidazolides (eg obtained from carbonyldiimidazole), activated esters or O-acyl ureas obtained from a carbodiimide such as a dialkylcarbodiimide particularly dicyclohexyl-carbodiimide. Preferably the amine is acylated with the acid in presence of a coupling agent such as 1,1'-carbonyldiimidazole, isobutylchloroformate or diphenylphosphinyl chloride.

The acids of formula (VII) may be prepared by methods known in the art eg from the piperazine derivatives of formula (II). For example a piperazine derivative of formula (II) may be reacted with an acid of formula $CH_2=CHR^1COOH$ by means of a Michael Reaction.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different steroisomeric forms. All steroisomeric forms are included within the invention. The compounds can be, for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors, particularly receptors of the $5-HT_{1A}$ type. In general, the compounds selectively bind to receptors of the $5-HT_{1A}$ type to a much greater extent than they bind to other receptors such as $\alpha_1$. The compounds can be used for the treatment of CNS disorders, such as anxiety in mammals, particularly humans. They may also be useful as antidepressants, hypotensives and as agents for regulating the sleep/wake cycle, feeding behaviour and/or sexual function and for treating cognition disorders.

The compounds of the invention are tested for $5-HT_{1A}$ receptor binding activity in rat hippocampal membrane homogenate by the method of B. S. Alexander and M. D. Wood, J Pharm Pharmacol, 1988, 40, 888–891. The compound of Example 5, which is a representative compound of the invention, had an $IC_{50}$ of 0.72 nM.

The compounds are also tested for $5-HT_{1A}$ receptor antagonism activity in a test involving the antagonism of 8-hydroxy-2-(di-n-propylamino)-tetralin (8-OH DPAT) syndrome in the rat. The compound of Example 5 exhibited a median effective dose of 0.3 mg/kg s.c.

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid. Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols, eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention.

EXAMPLE 1

Methyl pyruvate-3-nitrophenylhydrazone

A solution of methylpyruvate (31.8 g, 0.312 mol) in water-ethanol (10:1, 100 ml) was slowly added to a hot solution of 3-nitrophenylhydrazine hydrochloride (59.2 g, 0.312 mol) and sodium acetate (28.0 g, 0.34 mol) in water and ethanol (5:7, 1200 ml). The mixture was stirred at room temperature for 2 h during which time a heavy yellow precipitate developed. The precipitate was filtered, washed with cold water (2000 ml), and dried to give the product (66 g) as a yellow solid.

EXAMPLE 2

Methyl 4-nitroindole-2-carboxylate

The product of Example 1 (66 g, 0.278 mol) and polyphosphoric acid (1000 g) were stirred slowly as the temperature was raised to 90° C., at which point an exotherm occurred. The reaction mixture turned orange/brown and its viscosity increased. Further polyphosphofic acid (200 g) was added and the reaction mixture was stirred vigourously keeping the temperature below 100° C. by ice cooling. After 1 h, the mixture was poured into an ice/water mixture (5000 ml) and extracted into ethyl acetate (2 ×1500 ml). The extracts were washed with dilute aqueous sodium hydroxide (1000 ml), dried ($MgSO_4$), and evaporated in vacuo to give a mixture of methyl 4-nitroindole-2-carboxylate and methyl 5-nitroindole-2-carboxylate (total weight=45.6 g) as a grey yellow solid. This isomeric mixture was used without separation as the starting material in Example 3.

EXAMPLE 3

Methyl 4-aminoindole-2-carboxylate

Ammonium formate (63 g, 1.00 mol) was added cautiously to a suspension of the product of Example 2 (45.6 g, 0.207 mol) and 10% palladium on charcoal (5 g) in methanol (700 ml) under an argon blanket at 45° C. The mixture was stirred for 4 h, cooled to room temperature, and after 18 h filtered and evaporated in vacuo to give a dark brown semi-solid. This was taken up into acetonitrile (500 ml), filtered (to remove ammonium formate) and evaporated in vacuo to give a dark brown gum. Purification by column chromatography [silica; ethyl acetate-hexane (1:10 to 1:1)] gave the product (9.5 g) as a grey solid.

EXAMPLE 4

Methyl 4-(1-piperazinyl)indole-2-carboxylate

A mixture of the product of Example 3 (9.5 g, 0.051 mol), bis(2-chloroethyl)amine hydrochloride (10.6 g, 0.06 mol), and potassium carbonate (8.3 g, 0.06 mol) in anhydrous dimethylformamide (30 ml) was heated at 110° C. under argon. Further addition of bis(2- chloroethyl)amine hydrochloride (5.5 g, 0.031 mol) and potassium carbonate (4.2 g, 0.031 mol) were made after 7 h and 16 h. After another 6 h, the reaction mixture was poured into dilute potassium carbonate solution (400 ml) and extracted with ether (3×300 ml) and ethyl acetate (2×250 ml). The extracts were combined, dried ($MgSO_4$), and washed with water (2×200 ml). Evaporation of the solvent in vacuo gave a solid which was recrystallised from ether to give the product (5.0 g) as off-white crystals, m.p. 177°–180° C.

EXAMPLE 5

4-[4-(4-Azepan- 1-yl-4-oxo-3-phenylbutyl) piperazin-1-yl]-1H-indole-2-carboxylic acid methyl ester The product of Example 4 (1.30 g, 0.005 mol), 1-azepan-1-yl-4-chloro-2-phenylbutan-1-one (1.50 g, 0.005 mol), triethylamine (0.79 g, 0.0079 mol), and potassium iodide (0.2 g) were suspended in anhydrous dimethyl formamide (30 ml), stirred under argon for 3 h at 100° C., and poured into dilute potassium carbonate (300 ml). The mixture was extracted into ether (3×100 ml) and treated with excess dilute aqueous hydrogen chloride. The precipitate was filtered, washed with ether (3×100 ml), taken up into dilute sodium hydroxide solution (100 ml), and extracted into ether (3×100 ml). The extracts were dried ($MgSO_4$), and evaporated in vacuo to give a yellow crystalline glass. Purification by chromatography [alumina; ethyl acetate-hexane (2:3)] gave the product free base. The dihydrochloride salt of the product (1.35 g) was precipated as a colourless solid by the addition of ethereal hydrogen chloride to a solution of the free base in ethyl acetate, m.p. 152°–168° C. (Found: C, 57.4; H, 7.45; N, 8.7. $C_{30}H_{38}N_4O_3 \cdot 2HCl \cdot 3H_2O$ requires C, 57.2; H, 7.4; N, 8.9%).

EXAMPLE 6

1-Azepan-1-yl-2-phenyl-4-(4-quinolin-5-yl-piperazin-1-yl)-butan- 1-one

A mixture of 5-(1-piperazinyl)quinoline (932 mg, 4.37 mmol), potassium iodide (725 mg, 4.37 mmol), N,N-diisopropylamine (0.9 ml, 5.2 mmol), and 1-azepine- 1-yl-4-chloro-2-phenylbutan-1-one (1.22 g, 4.37 mmol) in dimethylformamide (20 ml) was heated at 110° C. for 16 h, cooled to room temperature, treated with water (150 ml), and extracted with ethyl acetate (2×50 ml). The extracts were washed with water (50 ml), dried ($Na_2SO_4$), and evaporated in vacuo. The residue was purified by chromatography [alumina; ethyl acetate-hexane (2:3)] to give the free base of the product (1.10 g). The dihydrochloride salt was a bright yellow crystalline solid, m.p. 216°–219° C. (Found: C, 63.4; H, 7.65; N, 10.15. $C_{29}H_{36}N_4O \cdot 2HCl \cdot 1¼H_2O$ requires C, 63.1; H, 7.4; N, 10.15%).

EXAMPLE 7

1-Azepan-1-yl-2-phenyl-4-(4-quinolin-8-yl-piperazin-1-yl)-butan-1-one

This compound was prepared from 8-(1-piperazinyl)-quinoline using the method described in Example 6. The one and a half hydrochloride salt of the product was obtained as sandy crystals, m.p. 223°–226° C. (Found: C, 64.7; H, 7.7; N, 10.2. $C_{29}H_{36}N_4O \cdot 1 ½HCl \cdot 1½H_2O$ requires C, 64.7; H, 7.6; N, 10.4%).

EXAMPLE 8

4-[4-(4-Azepan- 1-yl-4-oxo-3R- or 3S-phenylbutyl)-piperazin-1-yl]-1H-indole-2-carboxylic acid methyl ester Racemic 4-[4-(4-azepan- 1-yl-4-oxo-3-phenylbutyl) piperazin-1-yl]- 1H-indole-2-carboxylic acid methylester was resolved into the R and S enantiomers by high performance liquid chromatography on a chiral cell OD-R column (4.6×250 mm) using 60:40 mixture of acetonitrile: 0.5M sodium perchlorate buffer (pH 5.8). Detection was by U.V. (λ254 nm) flow rate 1 ml/minute. Under the conditions used the R enantiomer had a retention time of 32 min, and the S 4/min.

After work up the S-enantiomer was isolated as its dihydrochloride hemihydrate. mp 148°–149° C. Analysis Found: C, 61.8; H, 7.4; N, 9.5%. $C_{30}H_{38}N_4O_3.2HCl.0.5H_2O$ requires C, 61.6; H, 7.1; N, 9.6%.

The R enantiomer was isolated as its dihydrochloride three-quarter hydrate mp. 148°–149° C. Found: C, 61.5; H, 7.2; N, 9.5%. $C_{30}H_{38}N_4O_3.2HCl.0.75H_2O$ requires C, 61.2; H, 7.1; N, 9.5%.

EXAMPLE 9

1-Azepan-1-yl-4-[4-(1H-indol-4-yl)piperazin-1-yl]-2-phenylbutan-1-one

A suspension of 4-aminoindole (2.30 g, 0.017 moles), bischloroethylamine hydrochloride (3.49 g, 0.02 moles) and potassium carbonate (5.41 g, 0.02 moles) in butanol (50 ml) was heated at reflux under argon for 7 h. Further bischloroethylamine hydrochloride (0.70 g, 0.04 moles) and potassium carbonate (1.1 g 0.04 moles) was added, then the suspension was heated at reflux for 18 h. The solvent was evaporated in vacuo to give a brown gummy residue which was taken up into dilute hydrochloric acid (200 ml), washed with ethyl acetate (2×100 ml), made basic with potassium carbonate, extracted into dichloromethane (3×50 ml), dried ($MgSO_4$) then evaporated in vacuo to give a white solid which was triturated with ethyl acetate and dried to give 4-(1-piperazinyl)indole (0.78 g, 0.0038 moles) as white crystals.

A solution of the above product (0.70 g, 0.0035 moles), 1-azepine-1-yl-4-chloro-2-phenylbutan-1-one (1.12 g, 0.0040 moles), triethylamine (0.49 ml, 0.0035 moles) plus potassium iodide (0.2 g) in dimethylformamide (20 ml) was heated at reflux for 2 h then stirred at room temperature for 18 h under argon. The solvent was evaporated in vacuo to give a yellow oil which was taken up into ethyl acetate (50 ml), washed with dilute sodium carbonate solution (2×50 ml), dried ($MgSO_4$) then evaporated in vacuo to give a yellow oil. This was purified on an alumina column, eluting firstly with 30% ethyl acetate in hexane then with ethyl acetate alone to give the title compound (1.0 g) as a clear oil.

The above product was taken up into ethyl acetate then precipitated with ethereal hydrogen chloride to give the hydrochloride (0.75 g, 0.0014 moles) as a white solid m.p. 174°–177° C. (Found: C, 62.4; H, 7.6 N, 10.3%. $C_{28}H_{36}N_4O.2HCl.1.25H_2O$ requires C, 62.3; H, 7.6; N, 10.4%).

EXAMPLE 10

1-Azepan-1-yl-4-[4-(1H-indol-7-yl)piperazinyl-1-yl]-2-phenylbutan-1-one

A suspension of 7-aminoindole (4.10 g, 0.031 moles), bischloroethylamine hydrochloride (6.23 g, 0.035 moles) and potassium carbonate (9.66 g, 0.035 moles) in butanol (100 ml) was heated at reflux under argon for 6h. Further bischloroethylamine hydrochloride (3.0 g, 0.016 moles) and potassium carbonate (4.5 g, 0.016 moles) was added, then the suspension was heated at reflux under argon for 18 h. The solvent was evaporated in vacuo to give a deep purple residue which was taken up into dilute hydrochloric acid (300 ml), washed with ethyl acetate (2×100 ml), made basic with sodium hydroxide, extracted into dichloromethane, filtered, dried ($MgSO_4$) then evaporated in vacuo to a yellow oil. This was crystallised twice from ether to give 7-(1-piperazinyl)indole (2.07 g, 0.010 moles) as a grey/white solid.

A solution of 7-(1-piperazinyl)indole (1.00 g, 0.005 moles), 1-azepine-1-yl-4-chloro-2-phenylbutan-1-one (1.50 g, 0.0055 moles), triethylamine (0.50 g, 0.005 moles) plus potassium iodide (0.2 g) in dimethylformamide (30 ml) was heated at reflux under argon for 6 h. The solvent was evaporated in vacuo to give a brown residue which was taken up into dilute sodium carbonate solution (100 ml), extracted into ethyl acetate (2×100 ml), dried $MgSO_4$) then evaporated in vacuo to give a brown solid which was triturated with ethyl acetate (2×50 ml) and isopropanol (3×50 ml) to give the title compound (0.9 g) as a white solid.

The above product was taken up into dichloromethane (50 ml), then precipitated with ethereal hydrogen chloride to give the hydrochloride as a white solid, m.p. 138°–145° C. (Found: C, 65.7; h, 7.8; N, 10.8%. $C_{28}H_{36}N_4O.1.75HCl.0.25H_2O$ requires: C, 65.6; H, 7.52; N, 10.9%.)

We claim:
1. A compound of the formula

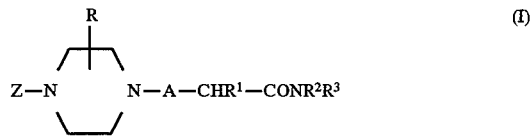

or a pharmaceutically acceptable acid addition salt thereof, wherein

A is a $C_1$–$C_2$ alkylene chain, optionally substituted by one or more $C_1$–$C_6$ alkyl groups, Z is a bicyclic nitrogen containing heteroaromatic radical selected from the group consisting of indolyl, isoindolyl, quinolinyl, isoquinolinyl, indazolyl and benzotriazolyl, which may be optionally substituted by one or two substitutents selected from $C_1$–$C_6$ alkyl, halogen, trifluoromethyl, nitro, cyano, oxo, hydroxy, $C_1$–$C_6$ alkoxy, hydroxy-$C_1$–$C_6$ alkyl, $C_1$–$C_6$ alkoxy-$C_1$–$C_6$ alkyl, $C_1$–$C_6$ alkanoyloxy-$C_1$–$C_6$ alkyl, $C_1$–$C_6$ acyl, $C_1$–$C_6$ acyl-$C_1$–$C_6$ alkyl, carboxamido, $C_1$–$C_6$ alkoxycarbonyl, amino, mono- or di-$C_1$–$C_6$ alkylamino;

R represents H or one or two same or different $C_1$–$C_6$ alkyl groups;

$R^1$ is an aryl radical or aryl-$C_1$–$C_6$ alkyl where aryl is phenyl or naphthyl, optionally substituted by 1 or 2 groups selected from $C_1$–$C_6$alkyl, $C_1$–$C_6$alkoxy, $C_1$–$C_6$alkylthio, cyano, amino, mono- or di-$C_1$–$C_6$alkylamino;

$R^2$ and $R^3$ together with the nitrogen atom to which they are both attached represent a saturated heterocyclic ring having 4 to 8 members, one of which can be an additional heteroatom selected from oxygen, sulfur, or nitrogen wherein said ring may be optionally substituted by $C_1$–$C_6$ alkyl, phenyl or phenyl-$C_1$–$C_6$ alkyl.

2. A compound as claimed in claim 1 in which A is ethylene.

3. A compound as claimed in claim 1 in which $R^2$ is hydrogen and $R^3$ is tert-alkyl or cycloalkyl.

4. A compound as claimed in claim 1 in which $NR^2R^3$ represents a piperidino or hexahydroazepino ring.

5. A compound as claimed in claim 1 in which Z is optionally substituted indolyl.

6. A pharmaceutical composition for use as a 5-$HT_{1A}$ antagonist comprising a compound claimed in claim 1 in association with a pharmaceutically acceptable carrier.

7. A compound of claim 1 which is 4-[4-(4-azepan-1-yl-4-oxo-3-phenylbutyl)piperazin-1-yl]-1H-indole-2-carboxylic acid methyl ester or a pharmaceutically acceptable salt thereof.

8. A compound of claim 1 which is 1-azepan-1-yl-2-phenyl-4-(4-quinolin-5-yl-piperazin-1-yl)-butan-1-one or a pharmaceutically acceptable salt thereof.

9. A compound of claim 1 which is 1-azepan-1-yl-2-phenyl-4-(4-quinolin-8-yl-piperazin-1-yl)-butan-1-one or a pharmaceutically acceptable salt thereof.

10. A compound of claim 1 which is 4-[4-(4-azepan-1-yl-4-oxo-3R-phenylbutyl)- piperazin-1-yl]-1H-indole-2-carboxylic acid methyl ester, or a pharmaceutically acceptable salt thereof.

11. A compound of claim 1 which is 4-[4-(4-azepan-1-yl-4-oxo-3S-phenylbutyl)- piperazin-1-yl]-1H-indole-2-carboxylic acid methyl ester, or a pharmaceutically acceptable salt thereof.

12. A compound of claim 1 which is 1-azepan-1-yl-4-[4-(1H-indol-4-yl)piperazin-1-yl]-2-phenylbutan-1-one or a pharmaceutically acceptable salt thereof.

13. A compound of claim 1 which is 1-azepan-1-yl-4-[4-(1H-indol-7-yl)piperazinyl-1-yl]-2-phenylbutan-1-one or a pharmaceutically acceptable salt thereof.

* * * * *